(12) United States Patent
Merrill, II et al.

(10) Patent No.: US 7,812,939 B2
(45) Date of Patent: Oct. 12, 2010

(54) SPECTROMETRIC MEASUREMENTS DURING BLENDING / MIXING

(75) Inventors: Dennis Merrill, II, New Glarus, WI (US); Matthew Daniel Ebersole, Sun Prairie, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 857 days.

(21) Appl. No.: 11/703,892

(22) Filed: Feb. 7, 2007

(65) Prior Publication Data

US 2007/0188753 A1    Aug. 16, 2007

Related U.S. Application Data

(60) Provisional application No. 60/773,069, filed on Feb. 13, 2006.

(51) Int. Cl.
*G01N 21/00* (2006.01)
(52) U.S. Cl. ....................................................... 356/73
(58) Field of Classification Search ................. 356/326; 73/509; 366/142
See application file for complete search history.

(56) References Cited

U.S. PATENT DOCUMENTS

| | | | |
|---|---|---|---|
| 5,065,025 A | 11/1991 | Doyle | |
| 5,946,088 A | 8/1999 | Aldridge | |
| 6,490,035 B1 | 12/2002 | Folestad et al. | |
| 6,517,230 B1 | 2/2003 | Afnan et al. | |
| 6,595,678 B2 | 7/2003 | Folestad et al. | |
| 6,771,370 B2 | 8/2004 | Sevick-Muraca et al. | |
| 6,794,670 B1 | 9/2004 | Folestad et al. | |
| 6,837,107 B2 | 1/2005 | Geen | |
| 6,874,928 B2 | 4/2005 | Afnan et al. | |
| 6,891,621 B2 * | 5/2005 | Berg et al. | 356/477 |
| 7,402,426 B2 * | 7/2008 | Brown et al. | 435/288.7 |

* cited by examiner

*Primary Examiner*—Tarifur Chowdhury
*Assistant Examiner*—Abdullahi Nur
(74) *Attorney, Agent, or Firm*—DeWitt Ross & Stevens; Charles B. Katz; Michael C. Staggs

(57) ABSTRACT

A mixing bin for the blending of materials (e.g., pharmaceuticals, foodstuffs, etc.) bears a spectrometer which monitors the characteristics of the material being tumbled within the bin interior to thereby obtain an indication of the degree to which the material is mixed. An accelerometer also rides on the mixing bin with the spectrometer, and it monitors the position of the mixing bin as it rotates. The accelerometer measurements can then be used to trigger the taking and/or recordation of spectrometer measurements at times during which the material within the bin falls against the spectrometer's input window, thereby promoting greater accuracy in spectrometer measurements, and/or at the same bin position, thereby promoting greater uniformity between spectrometer measurements.

22 Claims, 2 Drawing Sheets

US 7,812,939 B2

SPECTROMETRIC MEASUREMENTS DURING BLENDING / MIXING

CROSS-REFERENCE TO RELATED APPLICATIONS

This application claims priority under 35 USC §119(e) to U.S. Provisional Patent Application Ser. No. 60/773,069 filed 13 Feb. 2006, the entirety of which is incorporated by reference herein.

FIELD OF THE INVENTION

This document concerns an invention relating generally to sensor devices and methods for determining the properties of substances during mixing, and more specifically to devices and methods for performing molecular spectrometry on substances during mixing.

BACKGROUND OF THE INVENTION

In many fields of industry, e.g., chemical/pharmaceutical manufacturing, food processing, metallurgy/materials engineering, etc., it is often necessary to blend several materials to attain some desired mixture. It may be necessary to monitor the properties of the mixture during blending to verify that the blending process is proceeding as planned. In some cases, it may be desirable to monitor changes in composition, phase, or other properties of the materials in the mixture, as can often occur where the mixture is reactive, or where it is heated or otherwise acted upon during blending. In other cases, it may simply be desirable to monitor the properties of the mixture during blending to confirm the degree of blending. As an example, pharmaceuticals are often prepared by blending very precise amounts of different materials until they are very uniformly and completely mixed, and to control time and costs, it is desirable to cease blending as soon as mixing appears to be sufficiently thorough. Further, blending can be quite time-consuming because it must often occur without the use of rotating impellers/vanes or other mechanical mixing aids in the mixing bin, since such structures can shear the mixture and cause undesirable changes in its properties. As a result, the materials being mixed might only be mixable by tumbling them in a mixing bin, with the mixing bin having sufficient free space (and a suitable tumbling speed) that the materials uniformly commingle over time as blending proceeds.

Molecular spectrometers are sometimes used to monitor the characteristics of the mixture, but spectrometric measurements can be difficult to obtain from one of the aforementioned mixing bins. Most spectrometers function by emitting reference light having known wavelength(s) and intensity into a window in the mixing bin, and then capturing the light scattered from (and/or transmitted through) the mixture, with the difference between the reference and measured light providing information regarding the characteristics of the mixture. However, where materials are tumbled in a mixing bin, the composition adjacent the window can constantly change: at one moment it may be a solid or liquid mixture which has fallen or splashed against the window, and at another moment it may be the air or other gas that occupies the free space within the bin. Since one generally wishes to know the characteristics of the mixture, not the free space, one is then left with the issue of when to take spectrometric readings: readings should be actuated, or should be observed, when the mixture falls against the bin window. But since the time at which the mixture falls against the window can vary depending on a number of factors—such as the caking/agglomeration (or viscosity/surface tension) of the mixture, the shape of the mixing bin, the volume of the mixture versus the volume of the free space, the rotational speed of the mixing bin, etc.—it can be difficult to determine when to actuate or observe spectrometric readings. This can in turn lead to less than optimal results in the measurement of mixture properties.

SUMMARY OF THE INVENTION

The invention, which is defined by the claims set forth at the end of this document, is directed to methods and devices which at least partially alleviate the aforementioned problems. Following is a brief summary which reviews some of the preferred features of the invention, with this summary referring to the accompanying drawings to enhance the reader's understanding. More details on the invention are provided elsewhere in this document.

Referring to FIG. 1A for a schematic view of an exemplary preferred version of the invention, a mixing bin 100 is shown, with the mixing bin 100 being coupled to a drive 102 (here merely depicted schematically as a drive shaft) which rotates the mixing bin 100 about at least one axis (here the central axis of the drive shaft 102). The mixing bin 100 has a bin interior 104 suitable for containing some substance to be mixed, and at least one bin port 106 through which the mixing substance 10 may be input into or removed from the bin interior 104. In FIG. 1A, the bin port 106 is shown capped by a port cap 108 bearing a molecular spectrometer 110 (to be discussed at greater length below), whereas a conventional mixing bin 100 usually has a simple plate- or lid-like port cap 108 situated atop its bin port 106 when the bin port 106 is to be closed. Thus, when a mixing substance 10 is placed within the mixing bin 100 through the bin port 106, the bin port 106 may be capped (whether by the spectrometer 110 or by another port cap 108), and the bin may be rotated at a rate sufficient to tumble the mixing substance 10 within the bin interior 104 (generally at 10-20 RPM), thereby mixing the mixing substance 10 within the mixing bin 100.

To analyze the composition and/or other characteristics of the mixing substance 10 during mixing, the spectrometer 110 takes spectrometric readings from the mixing bin 100 as it rotates. The molecular spectrometer 110 preferably includes a spectrometer housing 112 which at least substantially surrounds the molecular spectrometer 110, with the spectrometer housing 112 including a mounting face 114 which is adapted to affix to the mixing bin 100 so that the spectrometer 110 rides thereon as the mixing bin 100 rotates. This is exemplified by the arrangement of FIG. 1A, wherein the spectrometer mounting face 114 is defined by the port cap 108, though arrangements such as that shown in FIG. 2 (wherein the spectrometer mounting face 214 is attached to the mixing bin 200 away from the port cap 108) are also possible. The spectrometer 110 includes a spectrometer input window 116 to admit light from the bin interior 104 to the molecular spectrometer 110 for analysis, with the bin interior 104 being optically coupled to the spectrometer input window 116. This optical coupling of the spectrometer input window 116 to the bin interior 104 may be achieved in a variety of ways, as by situating the spectrometer housing 112 on the port cap 108 with the spectrometer input window 116 immediately adjacent the bin port 106 (as in FIG. 1A), such that the spectrometer input window 116 is aligned with the bin port 106 to view the bin interior 104. As another example, FIG. 2 illustrates optical coupling of the spectrometer input window 216 to the bin port 206 via a light pipe 230 (e.g., a fiberoptic cable or other light-transmitting conduit) which extends from the spectrometer input window 116 to the bin port 106 to allow the spectrometer 110 to image the bin interior 104. Note that to assist the spectrometer 110 in accurately monitoring the characteristics of the mixing substance 10 as it is mixed (and thereby monitoring the degree of mixing), the spectrometer input window 116 should image a region of the bin interior 104 onto which the mixing substance 10 tumbles as the mixing bin 100 is rotated; thus, for example, the spectrometer 110 in FIG. 1A obtains readings from a bin port 106 at the outer circumference of the mixing bin 100, as opposed to obtaining readings from a region closer to the rotational axis 102, since the mixing substance 10 usually does not reside at a selected region near the rotational axis 102 for an extended period of time during rotation of the mixing bin 100.

For greater accuracy in spectrometric readings, it is then desirable to take readings at the times during which the mixing substance 10 tumbles against the bin port 106 and into alignment with the spectrometer input window 116, as opposed to the times during which the mixing substance 10 has fallen (or is falling) out of alignment with the spectrometer input window 116. Since it can be difficult to time spectrometric readings at those moments when the mixing substance 10 is aligned with the spectrometer input window 116, an accelerometer 118 is mounted in fixed relation to the mixing bin 100 to rotate therewith, and the accelerometer readings are used to actuate spectrometric readings (and/or to record such readings) at those times when the mixing substance 10 is situated at the bin port 106. The accelerometer 118 is preferably associated with the spectrometer 110, as by situating it within the spectrometer housing 112, and more particularly on the control circuit board 120 for the spectrometer 110 (as schematically depicted in FIG. 1A). It could instead be provided elsewhere on the mixing bin 100 at a location spaced away from the spectrometer 110, as depicted in FIG. 2 (to be discussed below).

The accelerometer 118 preferably measures at least the amplitude of acceleration (and more preferably both amplitude and frequency) along two or more axes, e.g., in radial and tangential directions, as schematically depicted by the arrows within the accelerometer 118 of FIG. 1A. This information can then be used to determine when to actuate spectrometric measurements (and/or when to record such measurements), as exemplified by the exemplary accelerometer output shown in FIG. 1B, which is generated by the 2-axis accelerometer 118 of FIG. 1A at a variety of different mixing bin 100 orientations (illustrated at the top of FIG. 1B). The radially-oriented acceleration measurements (shown as the uppermost trace) experience maxima and minima as the accelerometer's radial axis of measurement is vertically aligned, since it is at these orientations that the accelerometer 118 experiences the greatest gravitational force (keeping in mind that the rotational speed of the mixing bin 100 is generally sufficiently low that centrifugal forces are negligible in comparison to gravitational forces). Similarly, the tangentially-oriented acceleration measurements (shown as the lower trace) experience maxima and minima at 90 degrees out of phase from the radial measurements, at the times that the accelerometer's tangentially-oriented axis of measurement is aligned vertically (parallel with the axis of gravitational forces). Thus, so long as the acceleration measurements from one or both of these axes can be correlated with the times at which the mixing substance 10 is in position for spectrometric measurement within the bin interior 104, spectrometer measurements can be actuated and/or recorded at these times so that the characteristics of the mixing substance 10 can be accurately monitored (with exemplary spectra being illustrated at the bottom of FIG. 1B at various times during rotation of the mixing bin 100). For example, it is seen from FIGS. 1A-1B that the mixing substance 10 falls against the spectrometer input window 116 when the mixing bin 100 is inverted, corresponding to minimum amplitude in the radially-oriented acceleration measurements. Thus, when amplitude minima are detected in the accelerometer's radially-oriented acceleration measurements (or when amplitude minima are seen to be impending, as predicted from monitoring of measurements), the spectrometer 110 can be actuated to spectrometrically sample the bin interior 104, thereby obtaining measurements from the mixing substance 10 adjacent the bin port 106, and thus adjacent the spectrometer input window 116. Alternatively, if the spectrometer 110 monitors the bin interior 104 continuously (or nearly so, e.g., with numerous samples per revolution of the mixing bin 100), the accelerometer measurements can be used to record only those measurements taken at or near the time when the mixing substance 10 is aligned with the spectrometer input window 116, or to otherwise "flag" (i.e., specially indicate) such measurements.

Since it can be desirable to occasionally change the direction of rotation of the mixing bin 100 to attain better mixing, the use of a 2-axis accelerometer 118, or an accelerometer 118 monitoring acceleration in 3 or more axes, is useful since the multiple axes can allow determination of the rotational direction of the mixing bin 100 (for example, by noting whether the tangential acceleration measurements in FIGS. 1A-1B lead or lag the radial measurements). Nevertheless, a unidirectional (1-axis) accelerometer may be used rather than an n-axis accelerometer (where n>1) so long as the axis along which acceleration is measured at least gives an accurate indication of when the mixing substance 10 is in position for spectrometric measurement.

As implied above, it can be useful to utilize a data recorder, e.g., an electronic memory for data storage, to record at least the spectrometer measurements, and also preferably the accelerometer measurements (at least at those times when the spectrometer measurements are recorded). Such a data recorder is exemplified in FIG. 1A by a personal computer 122, which may include a data recorder such as a hard drive, and/or a drive for recording data onto a disk, tape, memory card/stick, or other media. Alternatively, the data recorder could travel on the mixing bin 100 in association with the spectrometer 110, e.g., as part of the spectrometer control circuit board 120. Where the data recorder 122 is not situated on the mixing bin 100, it preferably receives data from the spectrometer 110 and/or accelerometer 118 by wireless means (e.g., by radio frequency or optical transmission) to avoid the need for a rotating pickup allowing transmission of data by wire from the rotating mixing bin 100 to its stationary environment. To illustrate, the spectrometer control circuit board 120 in FIG. 1A includes a wireless transmitter 124 which sends spectrometer and accelerometer data (shown in FIG. 1B) to a wireless receiver 126 in communication with the personal computer 122 for storage by the data recorder therein.

In operation, the mixing bin 100 is rotated about at least one axis, and the spectrometer 110 can be actuated to sample the bin interior 104 (and/or the data recorder 122 can be actuated to record spectrometer measurements) at or near those times that the accelerometer measurements correlate with the times that the mixing substance 10 is against the bin port 106, or is otherwise in alignment with the spectrometer input window 116. The correlation between accelerometer measurements and spectrometer sampling times can be set observationally, e.g., in the exemplary system of FIGS. 1A-1B, one can simply program the system such that spectrometer measurements are captured at or near the time when the mixing bin 100 is inverted, such that the mixing substance 10 falls onto the bin port 106 and against the spectrometer input window 116. In these circumstances, it must be kept in mind that depending on factors such as the size of the mixing bin 100 and its rotational speed, the amount of the mixing substance 10 therein and its flow characteristics, etc., the mixing substance 10 may not fall against the spectrometer input window 116 at precisely the time when the mixing bin 100 of FIG. 1A is inverted; in particular, there may be a slight lag before the mixing substance 10 falls against the spectrometer input window 116. While such lags and similar factors can be estimated in order to set the time at which the accelerometer measurements will trigger sampling and/or recording of spectrometric readings, a preferred method is to experimentally determine the best times for spectrometric reading/recording (as by monitoring the spectrometer 110 readings for maximum reading resolution, e.g., highest measured peak amplitudes and/or greatest area beneath the spectral plot), correlate these times to the accelerometer readings, and then use these accelerometer readings as trigger points thereafter. This could be done, for example, by monitoring spectrometer 110 and accelerometer readings for (as an example) the first several rotations of the mixing bin 100, and then using these readings to set trigger points on the accelerometer readings thereafter. Such trigger points for taking and/or recording spectrometric readings can then be maintained until the rotational speed and/or direction change, at which time new trigger points may be established. (New trigger points may also be established at such times that matter is added to or removed from the mixing bin 100, or in cases where the mixing substance 10 may undergo changes in flow characteristics during mixing, it may be desirable to periodically reestablish trigger points to account for such changes.)

However, a particularly preferred method of operation is to set trigger points not with the mixing substance 10 itself, but rather with a reference substance having similar flow characteristics. As an example, the mixing bin 100 may be loaded with a known quantity of a known reference substance (such as talc powder), and may subsequently be rotated while sampling and recording spectrometer measurements and accelerometer measurements. The reference accelerometer measurements which corresponding to the maximum reference spectrometer measurements (e.g., maximum spectra heights corresponding to talc, and/or maximum area under the spectral plot) can then be used as trigger points for subsequent mixing operations, at least where the same mixing bin 100, substance quantity, and rotational speed is used as for the reference substance. Similar trigger points can be experimentally determined for different mixing bins, different substance quantities, and different rotational speeds so that a reference table of trigger points can be established for later mixing operations: when some quantity of mixing substance 10 is chosen for mixing in a particular type of mixing bin 100 under certain mixing conditions, reference can be made to the table to establish appropriate trigger points at which accelerometer measurements should be used to sample and/or record spectrometer measurements. With sufficient data in the table, trigger points might even be interpolated if there are no prior tests with a reference substance which present an exact match in mixing conditions.

Further advantages, features, and objects of the invention will be apparent from the remainder of this document in conjunction with the associated drawings.

DETAILED DESCRIPTION OF PREFERRED VERSIONS OF THE INVENTION

Figure 1A:
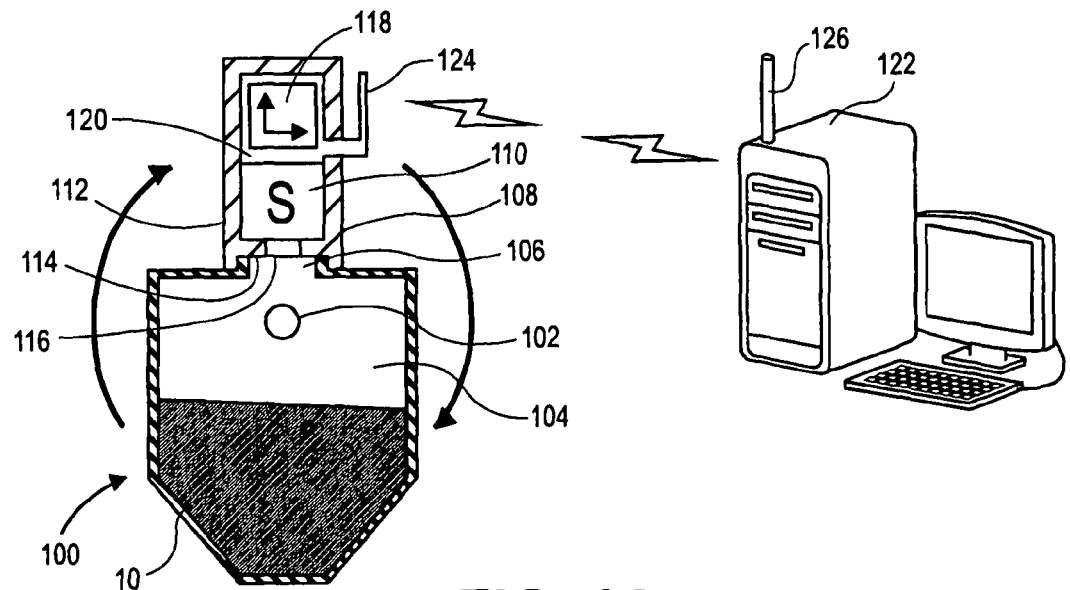
FIG. 1A is a schematic depiction of an exemplary mixing bin 100 which is tumbled about its rotational axis 102 to blend a mixing substance 10 within the bin interior 104, with the mixing bin 100 bearing a spectrometer 110 which takes measurements from the bin interior 104, and also bearing an accelerometer 118 which measures the acceleration (and velocity/position) of the mixing bin 100, with these measurements being wirelessly transmitted to a remote data recorder 122.
Figure 1B:
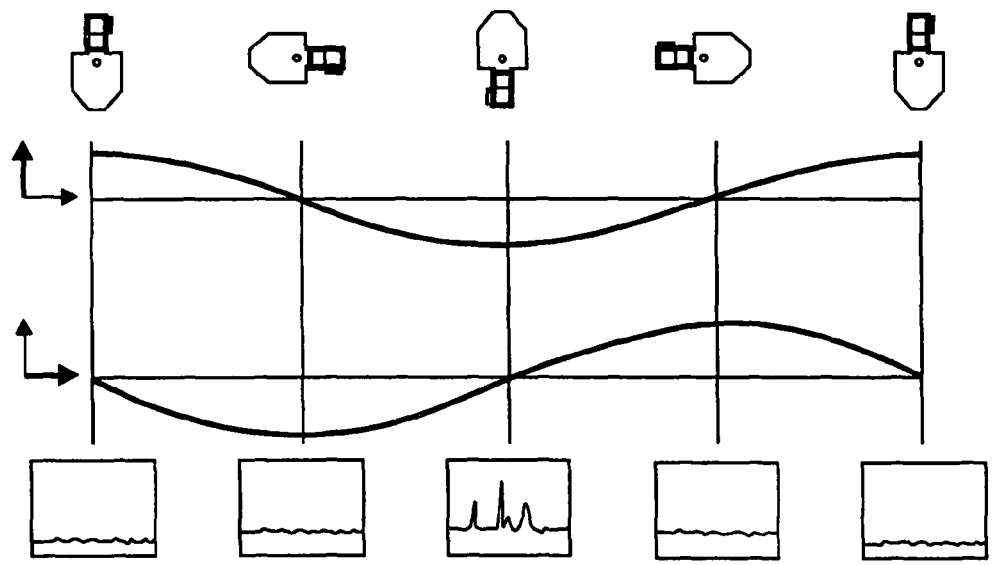
FIG. 1B is a schematic illustration of the measurements of the accelerometer 118 at each of its measurement axes, and also the measurements of the spectrometer 110, over a revolution of the mixing bin 100.

To expand on the details given in the foregoing Summary, the accelerometer 118 can be of any suitable type, e.g., potentiometric, LVDT, variable reluctance, capacitive, piezoelectric, etc., and is preferably chosen to have rapid response across the full range of rotational frequencies across which the mixing bin 100 is expected to operate (which usually tend to be rather low, on the order of 0.5 hz or less). As noted above, the accelerometer 118 can merely be a single-axis accelerometer, in which case it is preferably mounted to measure acceleration along an axis oriented perpendicular to the mounting face 114 of the spectrometer housing. However, multi-axis accelerometers 118 are preferred. It is also notable that the accelerometer 118 need not be provided in the spectrometer 110, and it could be situated elsewhere on or off of the mixing bin 100 (e.g., it could be situated on the motor drive shaft 102 rather than on the mixing bin 100).

Figure 2:
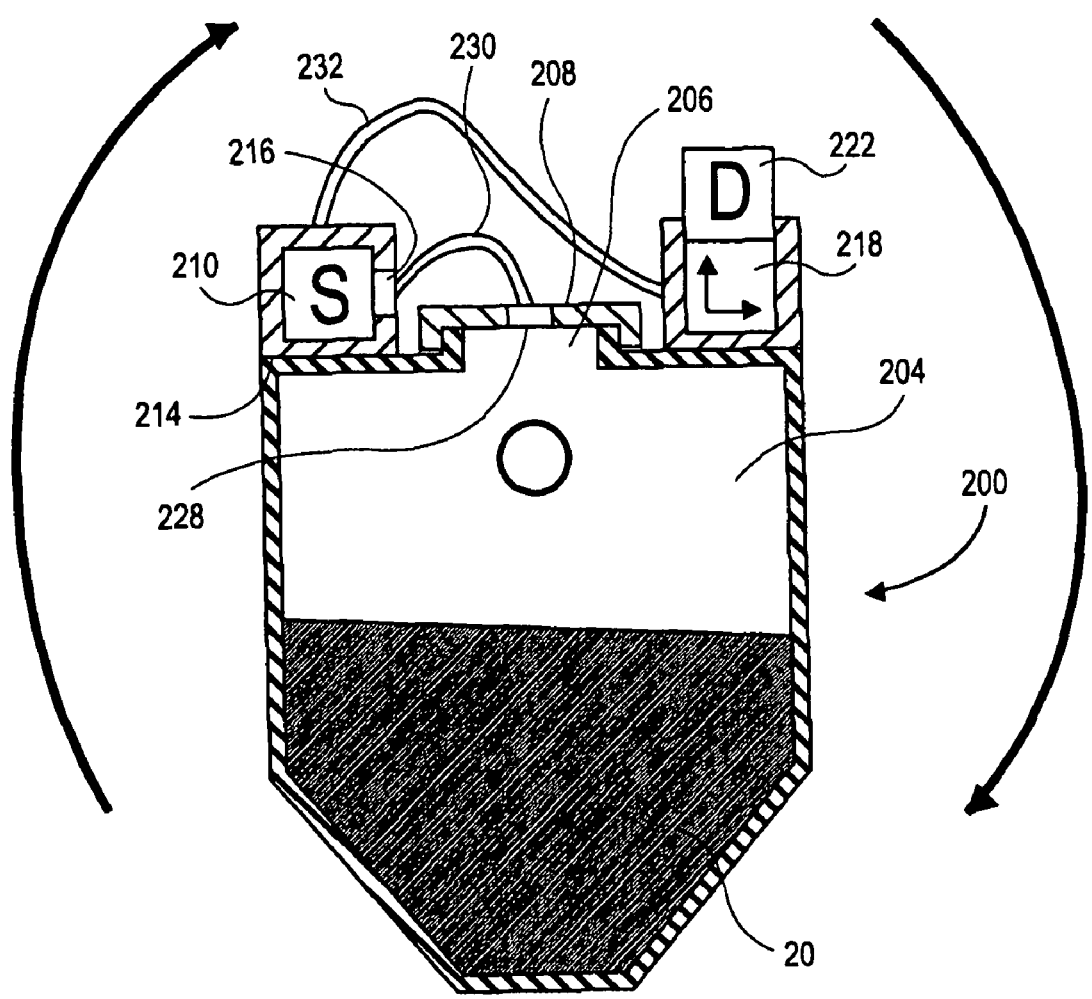
FIG. 2 is a schematic depiction of an exemplary mixing bin 200 which is tumbled about its rotational axis 202 to blend a mixing substance 20 within the bin interior 204, with the mixing bin 200 bearing a spectrometer 210 which takes measurements from the bin interior 204, and also bearing an accelerometer 218 which measures the acceleration (and velocity/position) of the mixing bin 200, with these measurements being recorded on an onboard data recorder 222.

It should be understood that the foregoing discussion and the associated drawings merely relate to exemplary preferred versions of the invention, and the invention can assume a wide variety of forms other than those described above and shown in the drawings. In particular, the mixing bin 100 and the associated spectrometer 110, data recorder 122, etc. can be configured in a variety of ways which differ significantly from the arrangement of FIG. 1A. An example is illustrated in FIG. 2, wherein a mixing bin 200 has a bin port 206 capped by a port cap 208, with the port cap 208 having a cap window 228 defined therein. A molecular spectrometer 210 is then affixed to the mixing bin 200 away from the bin port 206 and port cap 208, and it bears a spectrometer input window 216 which receives light from the cap window 228 and bin interior 204 via a light pipe 230 extending between the bin port 206 and the spectrometer input window 216. An accelerometer 218 (depicted as a 2-axis accelerometer) is also situated on the mixing bin 200, but unlike the arrangement of FIG. 1A, here the accelerometer 218 is provided separately from the spectrometer 210 and any spectrometer control circuit board therein. Rather, the accelerometer 218 communicates with the spectrometer 210 via a signal line 232 to actuate the taking and/or recordation of spectrometric measurements. A data recorder 222 is also provided on the mixing bin 200 in association with the accelerometer 218 to record measurements therefrom, and it may also record spectrometric measurements communicated via the signal line 232. Here, it is contemplated that the data recorder 222 might record data on some form of compact removable (and preferably rewritable) media, e.g., recordable discs or memory cards/sticks. As this version of the invention illustrates, the spectrometer need not directly image the bin interior and may do so remotely (via a light pipe or other transmission element); the data recorder need not be remote from the mixing bin; and the accelerometer need not be provided directly on or within the spectrometer (and may be provided, for example, in connection with any data recorder or other components riding with the mixing bin).

As another example of a variation, the bin port 106/206 to which the spectrometer input window 116/216 is optically coupled need not necessarily be a port which is sized and configured to allow the input and removal of the materials to be mixed, and rather it merely needs to be a port through which the bin interior 104/204 may be imaged. As an example, the spectrometer input window 116/216 might be optically coupled to a bin port 106/206 which takes the form of no more than a small passage which extends from the exterior of the mixing bin 100/200 to terminate in a window adjacent the bin interior 104/204, and which is situated adjacent a larger bin port 106/206 designed for loading and/or unloading of matter to be mixed.

It is also possible that the spectrometer 110/210 could obtain measurements from multiple points within the bin interior 104/204, e.g., from direct imaging of a bin port 106/206 (as in FIG. 1A) and also (or alternatively) via image transmission from one or more other bin ports 106/206 (as in FIG. 2). In this case, the spectrometer 110/210 might multiplex the various input paths from the bin ports 106/206, e.g., sequentially switch between the light pipes 230 or other media transmitting the images of the bin interior 104/204, so that the spectrometer 110/210 may sample each bin port 106/206 at a desired time. Alternatively, multiple spectrometers 110/210 might be provided, with each being dedicated to its own bin port 106/206.

Other sensors could be added to the arrangement to further enhance the measurements provided by the spectrometer 110/210 and accelerometer 118/218. As an example, looking to FIG. 1A, a load cell (e.g., strain gage) or similar sensor could be added on or in the spectrometer input window 116, or in the port cap 108 or other structure adjacent the location at which the bin interior 104/204 is spectrometrically imaged, so that the presence of the mixing substance 10/20 may be sensed when it tumbles thereon. The data from this sensor could then be used in addition to the position, speed, and/or acceleration/force data provided by the accelerometer 118/218 to determine the trigger points for taking and/or recording spectrometric readings. An appropriately configured load cell can beneficially be situated on the exterior of the mixing bin 100 to take measurements (e.g., on the window 116 outside the bin interior 104), or if situated inside the mixing bin 100, it may have such small size and low profile that it may not collect the mixing substance 10 thereon (which is an issue of concern for later cleaning of the mixing bin 100, particularly in fields such as pharmaceuticals and biotechnology where the mixing bin 100 must be free from impurities/contaminants). If fouling of a sensor and/or cleaning of the sensor and bin 100 are not of concern, a wide variety of sensors could be used inside the bin 100 to detect the presence of the mixing substance 10 at various locations along the bin wall. It is also possible that if data from the accelerometer 118 is not needed, such a sensor could be used in lieu of accelerometer data to actuate the taking and/or recording of spectrometer data.

It should also be understood that the operational techniques for the invention may also undergo significant modification. For example, as noted or implied above, it may in some cases be beneficial to vary rotational speed and/or direction to attain desired effects. To illustrate, periodic increases in rotational speed could be used to centrifugally "pin" the mixing substance 10/20 against some area of the interior walls of the mixing bin 100/200 so that the mixing substance 10/20 might be lifted, and then dropped within the bin interior 104/204 by a sudden decrease in rotational speed, to enhance mixing. As another example, the mixing substance 10/20 might desirably be centrifugally collected against the spectrometer input window 116/216 (or any other bin port 106/206 from which spectrometric readings are obtained) to control the period over which readings may be taken.

The accelerometer 118/218 can be used to effect spectrometer readings in respects other than merely actuating measurements and/or the recordation of measurements. As examples, accelerometer readings can be used (either by themselves or in combination with feedback from the spectrometer 110/210 itself) to adjust parameters such as the electronic gain of the spectrometer 110/210, the optical spot size (i.e., the size of the area imaged by the spectrometer 110/210), spectrometer resolution, spectrometer collection speed, and number of scans the spectrometer averages (if averaging is used). To illustrate, the optical spot size could initially be large, and could shrink after numerous revolutions, so that the spectrometric readings—which essentially "average" the characteristics of the mixing substance 10/20 over the imaged spot size area—will effectively begin by reflecting bulk measurements, and will later reflect measurements taken from small, discretely-sampled areas. As another illustration, some spectrometers will periodically recalibrate themselves by taking measurements from a reference substance, which may be present in the spectrometer itself. Here, the accelerometer readings could be used to trigger switching between measurements of the mixing substance 10/20 and the reference substance (e.g., the reference substance might be sampled when the accelerometer indicates that the mixing substance 10/20 is away from the bin port 106/206 and spectrometer input window 116/216). It can also be useful for later reference to use the accelerometer readings to "stamp" spectrometer readings with data such as the position, number of revolutions, rotational speed, etc. of the mixing bin 100/200, so that one can ascertain the state of the mixing bin 100/200 at the time a particular spectrometric reading was taken.

The accelerometer 118/218 can also be used for a variety of purposes in addition to (or other than) triggering spectrometer measurements. In particular, the accelerometer 118/218 is useful for monitoring and recordation of mixing schemes, e.g., it can be used to capture and record rotational speed (frequency) and direction(s) during mixing operations. It may be found that certain mixing schemes result in more rapid mixing of certain substances, since mixing can differ for different substances (e.g., it may depend on matters such as substance density, surface tension/adhesion and tendency to agglomerate, viscosity, etc.). Thus, by using the accelerometer 118/218 to monitor mixing schemes (i.e., factors such as rotational speed/direction and position), and using the spectrometer 110/210 to monitor the status of mixing (i.e., the characteristics of the mixing substance 10/20), one may be able to optimize mixing schemes to attain faster and more complete mixing. Feedback from the accelerometer 118/218 and spectrometer 110/210 can also be used to modify a mixing scheme during the scheme's execution; for example, if readings from the spectrometer 110/210 indicate that the mixing substance 10/20 is becoming well-mixed, the rotational speed of the mixing bin 100/200 (as measured by the accelerometer 118/218) can be decreased (or mixing can simply cease so that a new batch can be mixed in the bin 100).

In similar respects, it can also be useful to monitor the frequency of the accelerometer measurements for information relevant to measurement quality. For example, if rotational speed is so high that centrifugal effects might inhibit tumbling of the mixing substance 10/20 (e.g., the mixing substance 10/20 might be "pinned" to an interior wall of the mixing bin 100/200 away from the bin port 106/206), any spectrometric measurements might be discarded (or stored and flagged) as questionable.

Various preferred versions of the invention have been shown and described above to illustrate different possible features of the invention and the varying ways in which these features may be combined. The invention is not intended to be limited to the preferred versions of the invention described above, but rather is intended to be limited only by the claims set out below. Thus, the invention encompasses all different versions that fall literally or equivalently within the scope of these claims.

What is claimed is:

1. An analysis device for measuring properties of materials during mixing, the analysis device including:
   a. a molecular spectrometer;
   b. a spectrometer housing at least substantially surrounding the molecular spectrometer, the spectrometer housing having a spectrometer input window defined therein for admitting light; to be analyzed, wherein the spectrometer housing also includes an exterior mounting face, the mounting face being adapted for mounting to a mixing bin; and
   c. an accelerometer situated within the spectrometer housing and mounted in fixed relation to the mixing bin to rotate therewith and actuate the molecular spectrometer in response to accelerometer measurements generated by the accelerometer.

2. The analysis device of claim 1 wherein the accelerometer measurements include amplitude and frequency.

3. The analysis device of claim 2 further comprising a drive rotating the mixing bin about at least one axis.

4. The analysis device of claim 1 wherein the molecular spectrometer is continuously rotated about at least one axis.

5. The analysis device of claim 1:
   a. further comprising a data recorder; and
   b. wherein the data recorder records both:
      (1) spectrometer measurements from the molecular spectrometer, and
      (2) accelerometer measurements from the accelerometer, the accelerometer measurements being recorded at least substantially simultaneously with the spectrometer measurements,
   as the molecular spectrometer is continuously rotated about at least one axis.

6. The analysis device of claim 1:
   a. further comprising a data recorder; and
   b. wherein the data recorder records spectrometer measurements from the molecular spectrometer in response to accelerometer measurements from the accelerometer.

7. The analysis device of claim 6 wherein the data recorder wirelessly receives spectrometer measurements from the molecular spectrometer.

8. The analysis device of claim 1 wherein the accelerometer is an n-axis accelerometer, n being greater than or equal to 2, wherein the accelerometer measures acceleration about n axes.

9. The analysis device of claim 1 wherein:
   a. the spectrometer has a control board therein, and
   b. the accelerometer is situated on the control board.

10. The analysis device of claim 1 wherein:
the accelerometer measures acceleration along at least an axis oriented perpendicular to the mounting face.

11. The analysis device of claim 1:
   a. further comprising a light pipe extending from the spectrometer input window;
   b. wherein the spectrometer housing includes an exterior mounting face, the mounting face being adapted for mounting to a mixing bin.

12. The analysis device of claim 1 further comprising:
   a. a wireless transmitter in communication with the molecular spectrometer, the wireless transmitter wirelessly transmitting spectrometer measurements; and
   b. a wireless receiver remote from the wireless transmitter, the wireless receiver wirelessly receiving spectrometer measurements from the wireless transmitter.

13. The analysis device of claim 12 wherein the wireless transmitter:
   a. is also in communication with the accelerometer, and
   b. also wirelessly transmits accelerometer measurements.

14. The analysis device of claim 1:
   a. further comprising a mixing bin having a bin interior opening onto a bin port;
   b. wherein the spectrometer housing is adapted to mount to the bin with the spectrometer input window at the bin port, such that the spectrometer input window is aligned with the bin interior.

15. The analysis device of claim 14 further comprising a drive rotating the mixing bin about at least one axis.

16. The analysis device of claim 1 further comprising:
   a. a mixing bin having a bin interior opening onto a bin port, and
   b. a light pipe extending from the bin port to the spectrometer input window.

17. An analysis method comprising:
   a. situating a mixing substance in a mixing bin, the mixing bin including:
      (1) a molecular spectrometer situated thereon; and
      (2) an accelerometer mounted in fixed relation to the mixing bin to rotate therewith;
   b. rotationally driving the mixing bin about at least one axis; and
   c. recording spectrometer measurements from the molecular spectrometer in response to accelerometer measurements from the accelerometer.

18. The analysis method of claim 17 wherein the accelerometer measurements include amplitude and frequency.

19. The analysis method of claim 17 wherein:
   a. the molecular spectrometer includes a spectrometer input window opening onto the interior of the mixing bin; and
   b. spectrometer measurements are recorded in response to accelerometer measurements corresponding to any times at which the mixing substance rests in alignment with the spectrometer input window during rotation of the mixing bin.

20. The analysis method of claim 17 preceded by the steps of:
   a. situating a reference substance in the mixing bin;

b. rotationally driving the mixing bin about at least one axis;

c. recording both:
  (1) reference spectrometer measurements from the molecular spectrometer, and
  (2) reference accelerometer measurements from the accelerometer, the reference accelerometer measurements being recorded at least substantially simultaneously with the reference spectrometer measurements;

d. identifying the reference accelerometer measurements corresponding to the maximum reference spectrometer measurements; and e. removing the reference substance from the mixing bin, wherein the method of claim 17 is subsequently performed with spectrometer measurements being recorded in response to accelerometer measurements corresponding to the maximum reference spectrometer measurements.

21. The method of claim 20 further comprising the step of recording:
  a. the reference accelerometer measurements corresponding to the maximum reference spectrometer measurements, and
  b. the amount of the reference substance in the mixing bin.

22. The method of claim 20 further comprising the step of recording the type of mixing bin used when recording the reference spectrometer measurements and reference accelerometer measurements.

* * * * *